United States Patent [19]

Podszun et al.

[11] Patent Number: 4,937,144

[45] Date of Patent: Jun. 26, 1990

[54] DENTAL FILLERS

[75] Inventors: Wolfgang Podszun, Cologne; Jürgen Reiners, Leverkusen, both of Fed. Rep. of Germany

[73] Assignee: Bayer Aktiengesellschaft, Leverkusen, Fed. Rep. of Germany

[21] Appl. No.: 362,772

[22] Filed: Jun. 7, 1989

[30] Foreign Application Priority Data

Jun. 16, 1988 [DE] Fed. Rep. of Germany ....... 3820497

[51] Int. Cl.$^5$ .............................................. B32B 5/16
[52] U.S. Cl. .................................. 428/402; 523/115; 523/116; 524/307; 524/308; 524/311; 526/323.2
[58] Field of Search ................ 523/115, 116; 524/307, 524/308, 317; 526/323.2; 428/402

[56] References Cited

U.S. PATENT DOCUMENTS

| 4,396,377 | 8/1983 | Roemer et al. | 523/115 |
| 4,707,504 | 11/1987 | Walkowiak et al. | 523/115 |
| 4,711,913 | 12/1987 | Tatessian et al. | 523/115 |

*Primary Examiner*—Joseph L. Schofer
*Assistant Examiner*—Mark D. Sweet
*Attorney, Agent, or Firm*—Sprung, Horn, Kramer & Woods

[57] ABSTRACT

Cross-linked (meth)-acrylates having a particle size in the range from 0.01 to 10 μm which have a degree of swelling of 100 to 2,000% by weight and a degree of cross-linking of 50 to 100% by weight, relative to the polymer, are fillers for applications in the dental field.

5 Claims, No Drawings

DENTAL FILLERS

The invention relates to polymeric cross-linked (meth)-acrylates for applications in the dental field, their preparation and their use in dental materials.

Fillers for applications in the dental field can be employed, for example, in the production of false teeth, crowns, bridges, inlays, onlays, fillings and varnishes. In this connection, both inorganic fillers, such as finely ground quartz, and organic, polymeric fillers are used. In comparison to inorganic fillers, organic fillers lead to more homogeneous dental materials.

For example, cross-linked bead polymers having a particle size of 10 to 200 μm are mentioned as organic fillers (DE-A (German Published Specification) 2,849,280) which, however, are only slightly dissolved and swollen by the monomers of the polymerizable dental materials; there is thus still no complete homogeneity of the corresponding dental materials.

So-called IPN polymers (interpenetrating network) which are distinguished by high strength and resistance to solvents can be prepared by the swelling of cross-linked organic polymers (J. Polymer Science 12, 141 (1977) and J. Polymer Science 16, 583 (1978)).

Fillers for applications in the dental field made from bead polymers having a degree of swelling of 10 to 50% by weight are described in WO 82/02556. However, these bead polymers only have a low extent of cross-linking and do not achieve the high mechanical strength of highly cross-linked polymers.

Fillers for applications in the dental field containing polymeric cross-linked (meth)-acrylates having a particle size in the range from 0.001 to 10 μm have been found which are characterized in that they have a degree of swelling of 100 to 2,000% by weight and a degree of cross-linking of 50 to 100% by weight, in each case relative to the polymer.

(Meth)acrylates in the context of the present invention are esters of acrylic acid and/or methacrylic acid. Esters of methacrylic acid are preferred.

The poly(meth)acrylates according to the invention have a degree of cross-linking of 50 to 100% by weight, preferably of 85 to 100% by weight. The proportion of methacrylic acid esters which can form cross-linkages is defined as the degree of cross-linking.

Monomeric (meth)-acrylates which form cross-linkages are (meth)-acrylates having 2 or more, preferably 2 to 4, polymerizable double bonds in the molecule.

Monomeric (meth)-acrylates which form cross-linkages which may be mentioned, for example, are: ethylene glycol dimethacrylate, diethylene glycol dimethacrylate, triethylene glycol dimethacrylate, glycerol dimethacrylate, glycerol trimethacrylate, trimethylolpropane trimethacrylate, pentaerythritol dimethacrylate, pentaerythritol trimethacrylate, pentaerythritol tetramethacrylate, derivatives of bisphenol A, such as bisphenol A dimethacrylate and bisphenol A diglycol dimethacrylate, urethane methacrylates which can be prepared by reaction of diisocyanates and hydroxyalkyl methacrylates, such as

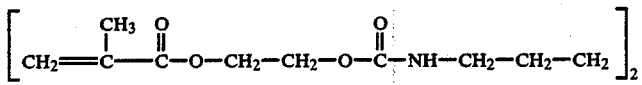

and reaction products of polyols, diisocyanates and hydroxyalkyl methacrylates (DE-A (German Published Specification) 3,703,080, DE-A (German Published Specification) 3,703,130 and DE-A (German Published Specification) 3,703,120).

Monomeric (meth)-acrylates which form cross-linkages are preferred, such as: ethylene glycol dimethacrylate, diethylene glycol dimethacylate, triethylene glycol dimethacrylate and glycerol dimethacrylate.

Monomeric (meth)-acrylates which form no cross-linkages which may be mentioned, for example, are: $C_1$-$C_{12}$-, preferably $C_1$-$C_4$-alkyl methacrylates, such as methyl methacrylate, ethyl methacrylate, n-propyl methacrylate, iso-propyl methacrylate, n-butyl methacrylate and t-butyl methacrylate, hydroxyalkyl ($C_1$-$C_4$) methacrylates, such as 2-hydroxyethyl methacrylate, 2-hydroxypropyl methacrylate, diethylene glycol monomethacrylate, triethylene glycol monomethacrylate, alkoxy ($C_1$-$C_4$) alkyl methacrylates, such as 2-methoxyethyl methacrylate, 3-methoxybutyl methacrylate and ethyl triglycol methacrylate.

Preferred monomeric (meth)-acrylates which form no cross-linkages are, for example: methyl methacrylate, ethyl methacrylate and 2-hydroxyethyl methacrylate.

The monomeric (meth)-acrylates are known per se and can be prepared, for example, by the reaction of (meth)-acryloyl chloride with the corresponding alcohols.

It is possible, of course, that the (meth)acrylates according to the invention form copolymers with further monomers. For example, the copolymers with styrene, α-methylstyrene, acrylonitrile and vinyl acetate may be mentioned here. In these cases, the proportion of the comonomer is 0 to 40, preferably 0 to 20, % by weight, relative to the polymer.

The degree of swelling is taken to mean the ability of the poly(meth)acrylates according to the invention to absorb liquid. The degree of swelling is measured by the ability to absorb tetrahydrofuran at 20° C. The poly(meth)acrylates according to the invention have an absorption of tetrahydrofuran of 50 to 2,000% by weight, preferably of 100 to 1,000% by weight, relative to the polymer.

The poly(meth)acrylates according to the invention in general have an average particle diameter of 0.01 to 10 μm, preferably of 0.05 to 5 μm.

Preferably, the poly(meth)acrylates according to the invention have a gel content of 90 to 100% by weight, preferably of 95 to 100% by weight, relative to the polymer. In the context of the present invention, according to the definition the gel content is taken to mean the proportion of the polymer which is not soluble at 20° C. using THF as the solvent. The gel content is a characteristic quantity for the cross-linking actually occurring.

The poly(meth)acrylates according to the invention preferably have an active surface area of 20 to 600 $m^2/g$, preferably of 50 to 300 $m^2/g$ (measured by the BET method).

A process for the preparation of the poly(meth)acrylates according to the invention for applications in the dental field has also been found which is characterized in that monomeric (meth)-acrylates which form cross-linkages and, if appropriate, (meth)-acrylates which form no cross-linkages and, if appropriate, further co-monomers are polymerized in the presence of an organic solvent having a solubility parameter of 8 to 15 [cal$^{0.5}$ cm$^{-1.5}$], the monomer content of (meth)-acrylates which form cross-linkages being 50 to 100% by weight.

Organic solvents can be defined by the so-called solubility parameter (H. G. Elias, Makromolekule, p. 192–196 (1981)). Solvents having a parameter from 8 to 15 [cal$^{0.5}$ cm$^{-1.5}$], preferably from 8.5 to 12 [cal$^{0.5}$ cm$^{-1.5}$], are used for the process according to the invention.

For example, the following solvents may be mentioned: amyl acetate, tetrachloroethane, toluene, ethyl acetate, tetrahydrofuran, benzene, trichloromethane, dichloromethane, methyl chloride, acetone, 2-butanone and tert.-butanol.

The amount of solvents in proportion to the monomeric (meth)-acrylates which can form cross-linkages is in the range from 1:1 to 1:100, preferably 1:2 to 1:20.

The polymerization process according to the invention is in general carried out in the temperature range from 50° to 250° C., preferably from 60° to 150° C. At the same time, the polymerization can be carried out continuously or batchwise.

The polymerization is in general carried out in the presence of initiators such as sensitizers or radical formers.

The initiators are in general employed in an amount from 0.01 to 3% by weight, preferably 0.1 to 1.5% by weight, relative to the total monomer.

Percompounds or radical-producing azo compounds can, for example, be used as polymerization initiators. Examples which may be mentioned are: aliphatic azodicarboxylic acid derivatives such as azobisisobutyronitrile or azodicarboxylic acid esters, peroxides such as lauroyl peroxide, succinyl peroxide, dibenzoyl peroxide, p-chlorobenzoyl peroxide, 2,4-dichlorobenzoyl peroxide, peroxides such as methyl ethyl ketone peroxide, methyl isobutyl ketone peroxide, cyclohexanone peroxide, acetylacetone peroxide, alkyl esters of peracids such as tert.-butyl perpivalate, tert.-butyl peroctoate, tert.-butyl perbenzoate, tert.-butyl perisononoate, mono-tert.-butyl permaleate, tert.-butyl peracetate, percarbonates such as dicyclohexyl and diisopropyl percarbonate, dialkyl peroxides such as di-tert.-butyl peroxide, dicumyl peroxide, hydroperoxides such as tert.-butyl or cumene hydroperoxides, monoperisophthalic acid or acetylcyclohexanesulphonyl peroxide.

A suspension of the filler in general results in the polymerization according to the invention. The isolation of the filler can be carried out, for example, by evaporating the solvent, for example in a spray drying process.

The fillers according to the invention are used as components for dental materials. They are readily wettable, easily dispersible and can be incorporated into dental monomers in a simple manner. Preferred dental monomers which may be mentioned, for example, are: methyl methacrylate, ethylene glycol dimethacrylate, diethylene glycol dimethacrylate, triethylglycol dimethacrylate, bisphenol-A diglycidyl dimethacrylate and mixtures of the monomers mentioned.

Preferred dental materials are comprising 5–35 parts by weight of the fillers according to the invention, 40–90 parts by weight of the monomer and 0,1–10 parts by weight of additives like accelerators, pigments and stabilizers which are known per se.

For the preparation of artificial teeth a mixture of 10–25% by weight of the filler according to this invention, 50–60% by weight of Bisphenol-A-diglycidyl-dimethacrylate, 25≧30% by weight of triethylene glycol dimethacrylate and 0,5% by weight of dibenzoyl-peroxide is especially preferred.

Application forms in the dental field, e.g. false teeth, crowns or fillings which contain the fillers according to the invention are distinguished by high mechanical strength, especially by high resistance to abrasion and high transparency.

EXAMPLE 1

1,800 g of 2-butanone, 200 g of ethylene glycol dimethacrylate and 2 g of dibenzoyl peroxide are weighed into a 3 l glass reactor which is equipped with a stirrer blade, reflux condenser, internal thermometer, gas inlet and gas outlet tube. The mixture is refluxed for 2 hours with stirring at 300 rpm and with nitrogen flushing. An easily stirrable suspension is formed. 190 g of fine powder can be obtained from this by spray drying. The average particle size (measured by laser correlation spectroscopy) is 700 nm, the gel content is 98.4%, the degree of swelling (measured in THF) is 310% and the BET surface area is 155 m$^2$/g.

EXAMPLE 2

Example 1 is repeated employing triethylene glycol dimethacrylate instead of ethylene glycol dimethacrylate. 196 g of fine powder having a particle size of 500 nm, a gel content of 95.8%, a degree of swelling of 690% and a BET surface area of 120 m$^2$/g are obtained.

EXAMPLE 3

Example 1 is repeated employing trimethylolpropane trimethacrylate instead of ethylene glycol dimethacrylate. 192 g of powder having a particle size of 900 nm, a gel content of 97.1% and a degree of swelling of 120% are obtained.

EXAMPLE 4

500 g of glycerol dimethacrylate and 5 g of dibenzoyl peroxide in 2,000 g of 2-butanone are reacted by the procedure indicated in Example 1. 475 g of powder having a particle size of 350 nm, a gel content of 97.3%, a degree of swelling of 280% and a BET surface area of 128 m$^2$/g are obtained.

EXAMPLE 5

Polymerizable composition 104 g of polymer from Example 1, 248 g of bis-GMA, 152 g of triethylene glycol dimethacrylate and 2.1 g of dibenzoyl peroxide are kneaded in a laboratory kneader in the course of 30 minutes. The resulting composition is stored at 35° C. for 5 hours. A transparent, non-tacky, dough-like paste is obtained.

EXAMPLE 6

Polymerizable composition 36 g of polymer from Example 1, 120 g of the reaction product of 2,2,4-trimethylhexamethylene diisocyanate and 2 mol of 2-hydroxyethyl methacrylate 1,6-bis-(methacryloyloxyethoxycarbonylamino)-2,2,4-trimethyl-hexane and 0.64 g of dibenzoyl peroxide are kneaded to a composition as described in Example 5.

EXAMPLE 7

20 g of polymer from Example 1, 60 g of bis-GMA, 30 g of triethylene glycol dimethacrylate, 10 g of 4-methoxybutyl methacrylate and 0.5 g of dibenzoyl peroxide are kneaded to a composition as described in Example 5.

It will be understood that the specification and examples are illustrative but not limitative of the present invention and that other embodiments within the spirit and scope of the invention will suggest themselves to those skilled in the art.

What is claimed is:

1. A polymeric cross-linked (meth)-acrylate having a particle size from about 0.01 to 10 μm, a degree of swelling of about 100 to 2,000% by weight and a degree of cross-linking of about 50 to 100% by weight, in each case relative to the polymer.

2. A polymeric cross-linked (meth)-acrylate according to claim 1, having a gel content of about 90 to 100% by weight.

3. A polymeric cross-linked (meth)-acrylate according to claim 1, having an active surface area of about 20 to 600 m$^2$/g.

4. A polymeric cross-linked (meth)-acrylate according to claim 1, having a gel content of about 90 to 100% by weight and an active surface area of about 20 to 600 m$^2$/g, the (meth)-acrylate being glycol dimethacrylate.

5. A polymeric cross-linked (meth)-acrylate according to claim 1, having a degree of cross-linking of about 85 to 100% by weight.

* * * * *